US009539165B2

(12) United States Patent
Heller

(10) Patent No.: US 9,539,165 B2
(45) Date of Patent: Jan. 10, 2017

(54) ANTI-REFLUX/HEARTBURN TREATMENT DEVICE

(71) Applicant: Brian Heller, Edgewater, NJ (US)

(72) Inventor: Brian Heller, Edgewater, NJ (US)

( * ) Notice: Subject to any disclaimer, the term of this patent is extended or adjusted under 35 U.S.C. 154(b) by 0 days.

(21) Appl. No.: 15/206,723

(22) Filed: Jul. 11, 2016

(65) Prior Publication Data

US 2016/0317377 A1 Nov. 3, 2016

Related U.S. Application Data

(63) Continuation of application No. 14/058,593, filed on Oct. 21, 2013, now Pat. No. 9,421,145.

(51) Int. Cl.

| | |
|---|---|
| ***A61B 17/00*** | (2006.01) |
| ***A61H 7/00*** | (2006.01) |
| ***A61H 39/04*** | (2006.01) |

(52) U.S. Cl.

CPC .............. *A61H 7/001* (2013.01); *A61H 39/04* (2013.01); *A61H 2201/0103* (2013.01); *A61H 2201/0192* (2013.01); *A61H 2201/165* (2013.01); *A61H 2201/168* (2013.01); *A61H 2201/1619* (2013.01); *A61H 2201/1695* (2013.01)

(58) Field of Classification Search

CPC .............. A41F 9/002; A41F 3/02; A41F 9/00; A41F 9/025; A41F 9/02; A41F 5/32; A41F 7/007; A61H 2201/1621; A61H 2201/1626; A61H 2201/163; A61H 2201/165; A61H 2201/1657; A61H 2201/168; A61H 2201/1683; A61H 2201/1688; A61H 2201/169;A61H 2201/1695; A61H 2201/1671; A61H 2201/1673; A61H 2201/164; A61H 2201/1666; A61H 2011/00; A61H 2011/005; A61H 11/02; A61H 39/04; A61B 17/132; A61B 17/1322; A61B 17/1325; A63B 21/002; A63B 21/0023; A63B 21/04; A63B 21/055; A63B 21/0552; A63B 21/0555; A63B 21/0557; A63B 21/065; A63B 23/02; A63B 23/0205; A63B 23/023; A63B 71/08

See application file for complete search history.

(56) References Cited

U.S. PATENT DOCUMENTS

| | | | |
|---|---|---|---|
| 2,547,727 | A | 4/1951 | Zaras |
| 2,645,221 | A | 7/1953 | Carter |
| 3,578,773 | A | 5/1971 | Schultz |
| 4,592,342 | A | 6/1986 | Salmasian |
| 4,787,379 | A | 11/1988 | Yeh |
| 4,944,289 | A | 7/1990 | Matthews |
| 5,010,902 | A | 4/1991 | Rambo et al. |
| 5,115,769 | A | 5/1992 | Fiorini |
| 5,127,422 | A | 7/1992 | Colon |

(Continued)

*Primary Examiner* — Jonathan Miles

(74) *Attorney, Agent, or Firm* — Welsh Flaxman & Gitler LLC

(57) ABSTRACT

A device worn by a patient for maintaining pressure at appropriate points on a patient's abdomen for treating gastroesophageal reflux and heartburn. The pressure is applied by the utilization of two protrusions. The position of both of the protrusions can be adjusted laterally relative to one another to ensure that pressure is applied to the correct position on the patient's body. Alternatively, the protrusions can be inflated to a particular level, allowing the protrusions to apply pressure to the body.

1 Claim, 8 Drawing Sheets

(56) References Cited

U.S. PATENT DOCUMENTS

| | | | | |
|---|---|---|---|---|
| 5,275,284 | A | 1/1994 | Onotsky | |
| 5,310,402 | A | 5/1994 | Rollband | |
| 5,404,623 | A | 4/1995 | Smiedt | |
| 5,643,315 | A | 7/1997 | Daneshvar | |
| 5,695,520 | A | 12/1997 | Bruckner et al. | |
| 5,728,120 | A | 3/1998 | Shani et al. | |
| 5,848,981 | A | 12/1998 | Herbranson | |
| 6,193,740 | B1 * | 2/2001 | Rodriguez | A61F 9/04 606/204.15 |
| 6,274,786 | B1 | 8/2001 | Heller | |
| 6,497,641 | B1 | 12/2002 | Hinds | |
| 8,100,841 | B2 | 1/2012 | Rousso | |
| 2001/0041851 | A1 | 11/2001 | Peyton et al. | |
| 2003/0004446 | A1 | 1/2003 | Taylor | |
| 2003/0163176 | A1 * | 8/2003 | Bae | A61F 7/007 607/96 |
| 2004/0055076 | A1 * | 3/2004 | Yoo | A61F 7/02 2/338 |
| 2004/0077982 | A1 | 4/2004 | Reinecke | |
| 2006/0021202 | A1 | 2/2006 | English | |
| 2006/0142675 | A1 | 6/2006 | Sargent | |
| 2007/0299368 | A1 * | 12/2007 | McCarthy | A61H 1/0292 601/1 |
| 2008/0200853 | A1 | 8/2008 | Tielve | |
| 2009/0326427 | A1 * | 12/2009 | Kawahara | A61F 5/024 602/19 |
| 2010/0016768 | A1 | 1/2010 | Liu | |
| 2010/0279830 | A1 | 11/2010 | Snagg | |
| 2010/0312158 | A1 | 12/2010 | Lin | |
| 2013/0150221 | A1 | 6/2013 | Sibley | |
| 2014/0031861 | A1 | 1/2014 | Teeslink et al. | |
| 2014/0088352 | A1 | 3/2014 | Maurette | |
| 2014/0128788 | A1 | 5/2014 | Marshall | |
| 2015/0012037 | A1 | 1/2015 | Goldman et al. | |

* cited by examiner

ANTI-REFLUX/HEARTBURN TREATMENT DEVICE

CROSS-REFERENCE TO REL,ATED APPLICATION

This application is a continuation of U.S. patent application Ser. No. 14/058,593, filed Oct. 21, 2013, entitled “ANTI-REFLUX/HEARTBURN TREATMENT DEVICE”, now U.S. Pat. No. 9,421,145.

BACKGROUND OF THE INVENTION

1. Field of the Invention

The present invention is directed to a device for treating conditions such as gastroesophageal reflux, heartburn and hiatal hernias.

2. Description of the Related Art

Many people suffer from gastroesophageal reflux disorder (GERD). Gastroesophageal reflux disorder is a backward or return flow of gastric or intestinal contents into the esophagus. Heartburn is a symptom of this disorder.

This disorder arises when the lower esophageal sphincter between the stomach and the esophagus becomes lax, spastic, or is interfered with as result of a hiatal hernia. This allows gastric acid to move from the stomach into the esophagus. The gastric juices irritate the esophagus lining causing heartburn.

Common causes of this disorder include improper diet, obesity, pregnancy and a hiatal hernia. Treatment of this disorder typically includes a change in diet and/or the use of over-the-counter or prescription medications, such as antacids H2 blockers and proton pump inhibitors. Severe cases may require invasive anti-reflux surgery which often prove to be ineffective, with recurrence of this problem being common. Additionally, invasive anti-flux surgery can sometimes worsen the problem.

U.S. Pat. No. 6,274,786 to Heller describes a device for applying pressure to a patient’s abdomen to treat heartburn, GERD or a hiatal hernia. The device described in the ’786 patent includes an immobile protrusion or nub provided between an inner and outer layer of the device. The device is attached to a strap which encircles a patient’s body, allowing the protrusion or nub to apply pressure to an anatomical particular point on the patient’s abdomen to relive the symptoms of heartburn/reflux. Since it is of utmost importance that pressure be applied to the appropriate portion of the patient’s abdomen, and since the physiological structure of patients are different, it is of crucial importance that the protrusion or nub be applied to a particular portion of the patient’s abdomen. Due to the immobile nature of the protrusion, proper placement of the protrusion on the patient’s abdomen is difficult. Improper placement of the protrusion on the abdomen is ultimately ineffective in correcting the patient’s symptoms.

Chiropractors may treat heartburn, GERD and hiatal hernias by manually pressing down on the patient’s abdomen using a particular pressure and motion. This mechanical pressure serves to return the stomach to its correct position, thereby assisting in closing the cardiac sphincter in helping to reduce heartburn/reflux. It is very important pressure be applied to the appropriate position of the patient’s abdomen. This position is at a similar location that an acupuncturist would utilize to treat a patient’s heartburn. It has been found the application of pressure at locations such as Ren 12, Ren 13 and Ren 17, as well as when acupuncture needles are inserted therein, results in relief of heartburn. The Ren 12 point is located on the midline of the abdomen about the width of the thumb at the knuckle above the umbilicus. This is a very important point of the stomach, as according to Chinese methods, the application of pressure or acupuncture needles imparts tone to the stomach and the spleen. Ren 13 is a point on the midline of the abdomen several inches above the umbilicus. Ren 17 is located on the interior midline level with the fourth rib or intercostal space. The anatomical locations listed hereinabove are but examples to show that acupuncture needles and/or acupressure by a practitioner’s finger or hand are commonly utilized to relieve these and other symptoms. The device of the present invention is employed to delegate pressure to the upper abdominal region, thereby replacing the need for a needle or digital pressure.

SUMMARY OF THE INVENTION

It is, therefore, an object of the present invention to provide an anti-reflux/heartburn device to properly apply mechanical pressure to a patient’s body allowing the stomach to return to its correct position and closing the esophageal sphincter and inducing reduction in heartburn/reflux.

It is, therefore, another object of the present invention to provide an anti-reflux/heartburn device including a planar base section provided with first and second ends. First and second protrusions are provided on the planar base section. The first and second protrusions are separated from one another. A position changing device is provided on the planar base section for laterally altering the position of the first and second protrusions relative to one another on the planar base section. When the device is applied to a patient’s abdomen, the first and second protrusions are positioned to relieve heartburn and reflux.

It is, therefore, an object of the invention to provide relief for heartburn, gastroesophageal reflux disorder possibly caused by a hiatal hernia, poor diet, pregnancy or obesity.

It is another object of the invention to provide a low cost treatment for heartburn and/or gastroesophageal reflux disorder.

It is another object of the present invention to provide a non-invasive device for the treatment of heartburn and/or gastroesophageal reflux disorder.

It is a further object of the present invention to provide a device that assists in closing the cardiac sphincter.

It is another object of the present invention to treat heartburn and/or gastroesophageal reflux disorder in a non-chemical, non-surgical manner.

It is a further object of the present invention to provide a treatment for heartburn and/or gastroesophageal reflux disorder that is both simple to use and inexpensive.

It is yet a further object of the present invention to provide a treatment of heartburn and/or gastroesophageal reflux disorder in which the placement of a protrusion (or protrusions) of the device with respect to a particular point on a patient’s body can be easily changed without completely removing the device from around the patient’s torso.

It is a further object of the present invention to provide a device to properly apply mechanical pressure to the appropriate portion of a patient’s body using a bladder system for inflating and deflating the first and second protrusions provided on the planar base section to change the amount of pressure applied without adjusting the lateral position of the first and second protrusions.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Figure 1:
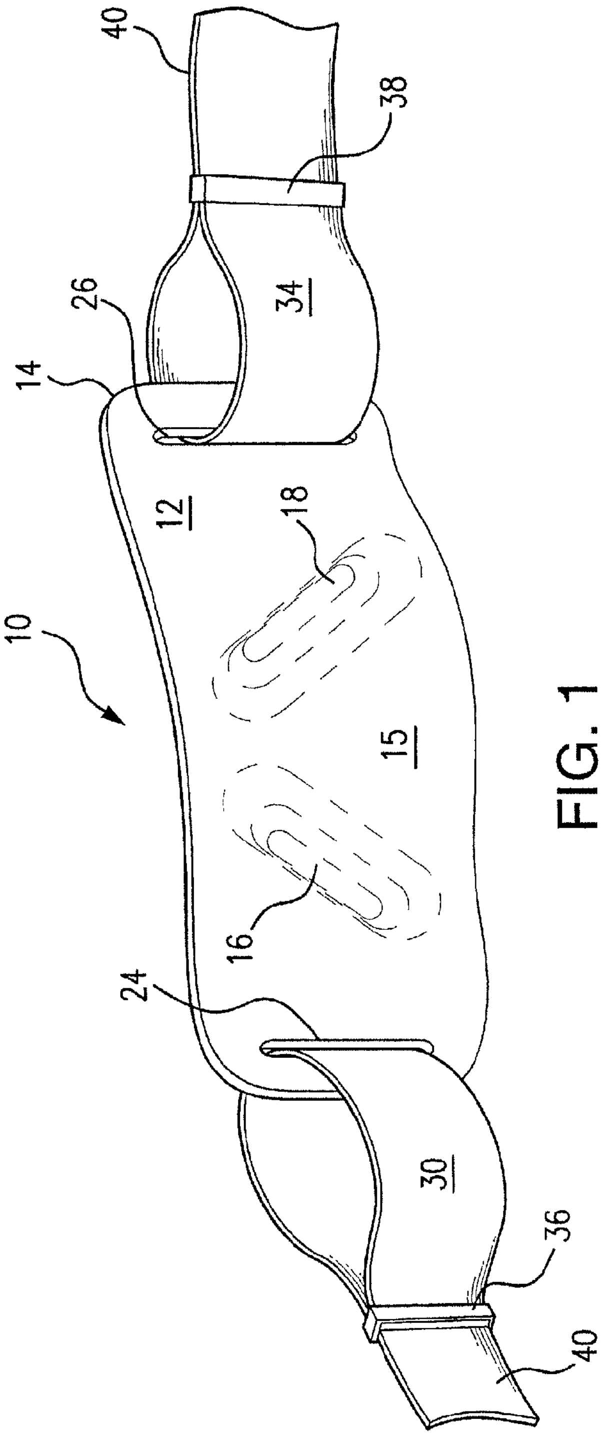
FIG. 1 is an elevational view of the present device for treating conditions such as gastroesophageal reflux, heartburn and hiatal hernias.
Figure 3:
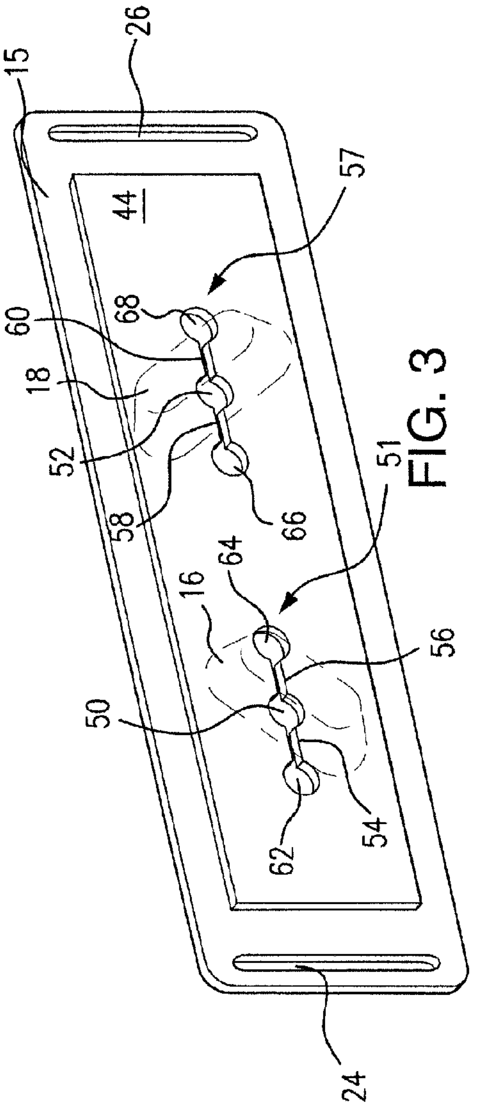
FIG. 3 is a perspective view of the base plate of a first embodiment of the present invention showing the adjustability feature of the protrusions.
Figure 4:
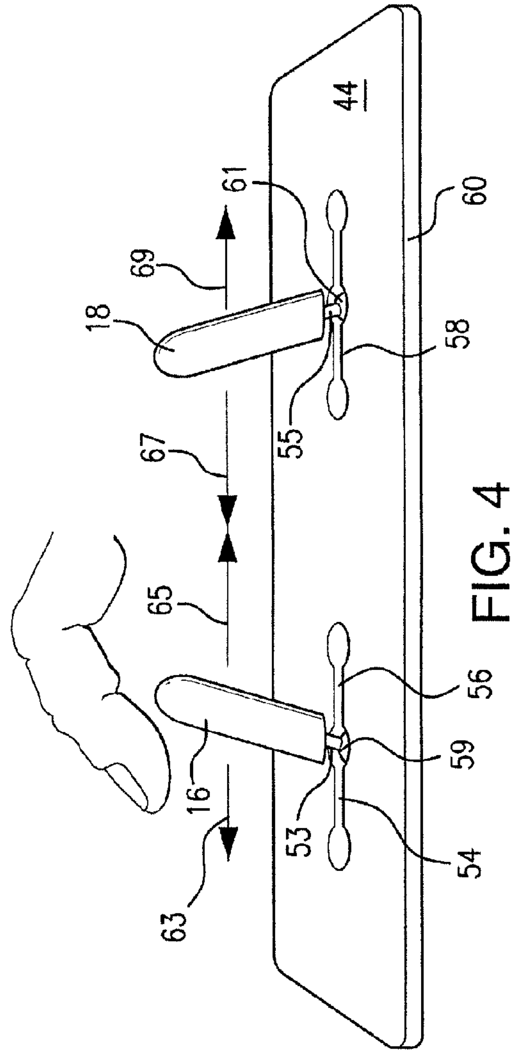
FIG. 4 is a side view of a portion of the base section shown in FIG. 3.
Figure 5:
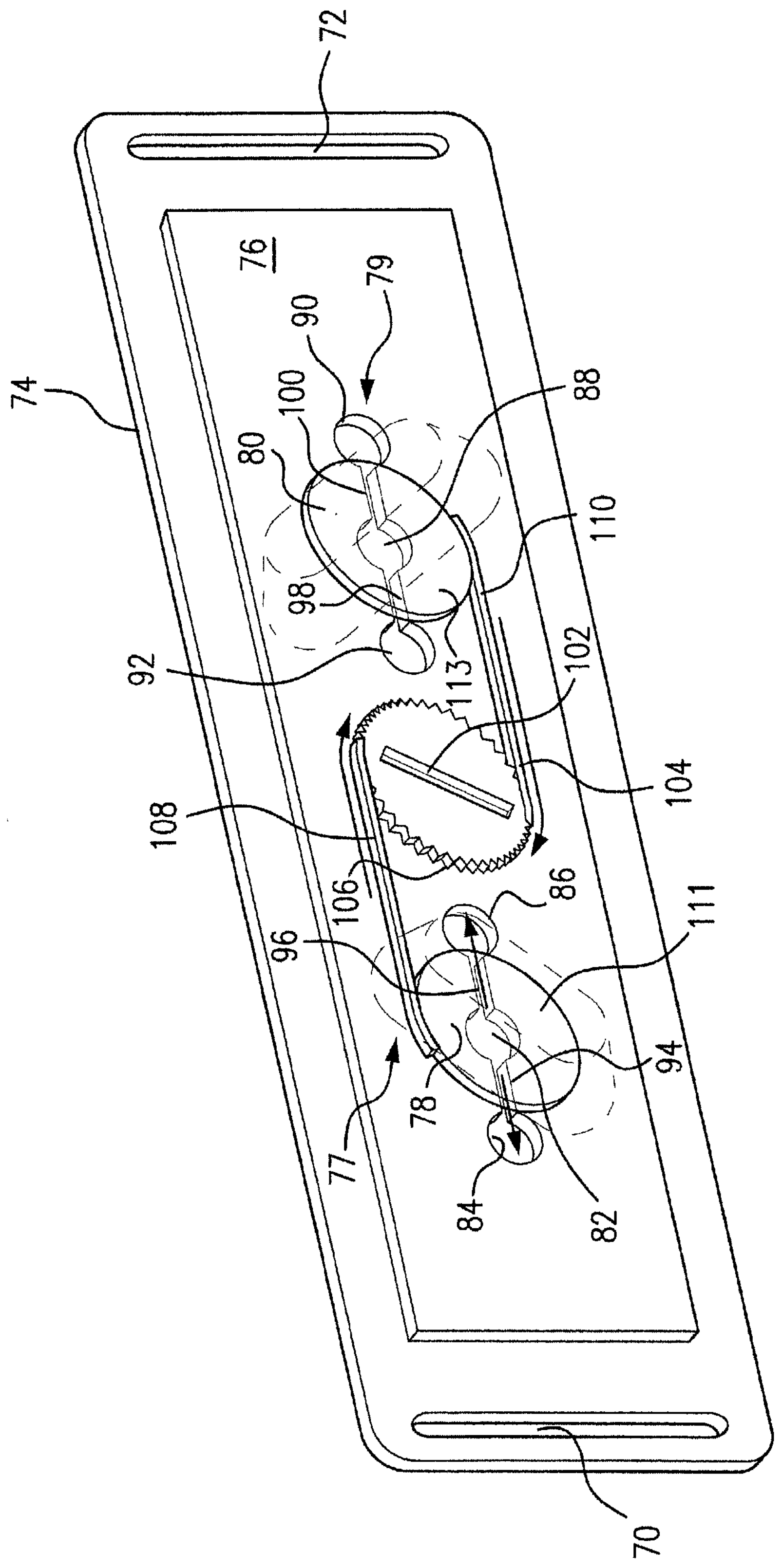
FIG. 5 is a perspective view of a second embodiment for adjusting the position of the protrusions.

The invention can be better understood with reference to the drawings. FIG. 1 shows a perspective view of the present invention 10 for treating conditions such as gastroesophageal reflux, heartburn and hiatal hernias. The present invention 10 includes two separate protrusions 16, 18 (shown in phantom) provided on a base section 15, as well as a position changing device provided on the base section 15, for laterally altering the position of the two separate protrusions 16, 18 relative to one another on the base section 15. Various position changing devices are illustrated in FIGS. 3, 4, 5 and 7 as will be subsequently explained. However, the position changing devices shown in FIGS. 3, 4 and 5 are not seen in FIGS. 1 and 2, as they are covered by a front layer 12. The base section 15 is preferably planar and made from a rigid material provided with some give or leeway. These protrusions 16, 18 are constructed from a semi-dense foam rubber or silicone material. However, it is appreciated that any material can be utilized which would apply pressure to an anatomical point on the human body. Each of the protrusions 16 and 18 can be provided with an interior endoskeleton 20 and 22 respectively for providing rigidity to the protrusions 16 and 18.

More particularly, the device 10 includes the base section 15 upon which are mounted the first and second protrusions 16, 18. A front layer 12 covers the front side 13 of the base section 15 and the protrusions 16, 18, while a back layer 14 covers the back side 17 of the base section 15. As such, the protrusions 16, 18 and the base section 15 are positioned between the front layer 12 and the back layer 14. Additionally, it is noted that the position changing devices shown in FIGS. 3, 4 and 5 are also positioned between the front layer 12 and the back layer 14. Both the front layer 12 and the back layer 14 are constructed from a clear silicon material which is slightly more rigid than the protrusions 16, 18 enabling the protrusions 16, 18 to more easily move in a lateral direction. Alternatively, the base section 15 is constructed from only a single layer of material, with the protrusions 16, 18 directly attached to the top of the base section 15.

Figure 2:
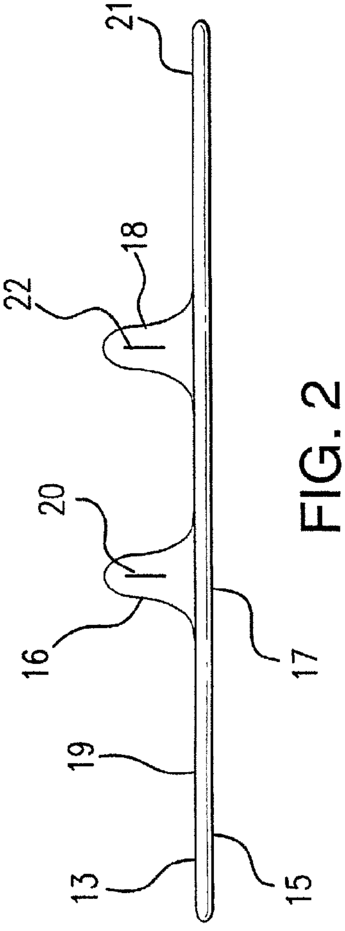
FIG. 2 is a side view of the protrusions of the present device shown in FIG. 1.

The protrusions 16, 18 are positioned on the planar base section 15 such that the first protrusion 16 is located closer to the first end 19 of the base section 15 and second protrusion 18 is located closer to the second end 21 shown in FIG. 2. The inclusion of two protrusions 16, 18 ensures that pressure is applied to more than one location on the patient's abdomen.

The protrusions 16, 18 are angled with respect to one another. In particular, each of the protrusions 16, 18 is elongated and therefore includes a long axis (substantially parallel to the plane in which the base section 15 lies and defining the length of the protrusion) and a short axis (substantially parallel to the plane in which the base section 15 lies and defining the width of the protrusion). As such, and in accordance with a preferred embodiment of the present invention, the protrusions are oriented such that the long axes of the respectively protrusions 16, 18 are oriented between 20° and 80° with respect to each other. However, it is appreciated lesser or greater angles can be employed. Alternatively, the protrusions can be constructed in many shapes, such as spherical in configuration.

As discussed above, the base section 15 upon which the protrusions 16, 18 are secured is positioned between the front layer 12 and the back layer 14 of the device 10 as illustrated in FIG. 1. The layers 12, 14 can be secured to one another by any suitable means such as by stitching, the use of adhesive or the like.

A band or belt 40 is constructed from soft material which is adjustable in length allowing the device to encircle a patient's torso. A first loop 30 of the belt 40 extends through an aperture 24 provided at one end of the device 10 and extends completely through the front and back layers 12, 14. A second loop 34 extends through an aperture 26 also extending completely through the front and back layers 12, 14. Loops 30, 34 are used to increase or decrease the length of the belt 40. A device such as a buckle 36 is preferably used for increasing or decreasing the length of the loop 30. Movement of the buckle 36 toward the base 15 section decreases the length of the loop 30, effectively increasing the length of the belt 40. Movement of the buckle 36 away from the base 15 increases the length of the loop 30, effectively decreasing the length of the belt 40. A device such as a buckle 38 is used for increasing or decreasing the length of the loop 34. Movement of the buckle 38 toward the base 15 decreases the length of the loop 34, effectively increasing the length of the belt 40. Movement of the buckle 38 away from the base 15 increases the length of the loop 34, effectively decreasing the length of the belt 40. The purpose of the belt and loop combination is to allow adjustability of the belt 40 when applied to the patient's torso, due to different sizes of the patients.

FIG. 3 illustrates one manner in which the relative position of the protrusions 16, 18 (shown in phantom) can be altered by changing the lateral position of the protrusions 16, 18 on the base section 15 having a portion 44 of its upper surface constructed from a material provided with some flexibility, such as rubber or foam. The protrusions 16, 18 may be selectively moved laterally across the surface of the base section 44 as will be subsequently explained.

As with the device shown with reference to FIGS. 1 and 2, the present invention 10 includes a base section 15 upon which are mounted the first and second protrusions 16, 18. Although FIG. 3 shows the device with the front and back layers removed, it is appreciated when the device is fully constructed for use the base section 15 would be situated between the front layer 12 and the back layer 14 shown in FIG. 1, positioning the protrusions 16, 18 therebetween.

As shown in FIG. 3, where the front layer and back layer are removed for the sake of clarity in explaining the invention, protrusions 16, 18 are provided on portion 44 of the base section 15. The base section 15 is provided with first and second channel arrangements 51, 57 for the retention and movement of the protrusions. The first channel arrangement 51 includes a center slot 50, a left slot 62 and a right slot 64. A passageway 54 is provided between the center slot 50 and the left slot 62. A passageway 56 is provided between the center slot 50 and the right slot 64. Similarly, the second channel arrangement 57 includes a center slot 52, a left slot 66 and a right slot 68. A passageway 58 is provided between the center slot 52 and the left slot 66. A passageway 60 is provided between the center slot 52 and the right slot 68. The protrusion 16 is retained within the first channel arrangement 51 and is therefore moveable under the control of a user between the center slot 50, the left slot 62 and the right slot 64 which are included in the base section 15. The first protrusion 16 moves within the passageway 54 as it moves between the center slot 50 and the left slot 62 under the control of the user. The first protrusion 16 moves within the passageway 56 as it moves between the center slot 50 and the right slot 64 under the control of the user. Similarly, the second protrusion 18 is retained within the second channel arrangement 57 and is therefore moveable under the control of a user between the center slot 52 and a left slot 66, as well as between the center slot 52 and a right slot 68. The second protrusion 18 moves within the passageway 58 as it moves between the center slot 52 and the left slot 66 under the control of the user. The second protrusion 18 moves within the passageway 60 as it moves between the center slot 52 and the right slot 68 under the control of the user.

Referring now to FIG. 4, the protrusion 16 is secured within the first channel arrangement 51 through the utilization of a retained ball 59 and a connector 53 attaching the protrusion 46 to the ball 59. In particular, the ball 59 is sized such that it is retained within the first channel arrangement 51 through friction due to the slight flexibility of the material of the portion 44 of base section 15, while the member 53 connects the ball 59, and ultimately the first channel arrangement 51 to the protrusion 16. In this way, the ball and protrusion are moved in controlled manner relative to the first channel arrangement 51. That is, the ball 59 moves between the center slot 50, the left slot 62 and the right slot 64 through passageways 54 or 56 to thereby move the protrusion 16 to various positions along the base section 15 adjacent the respective center slot 50, the left slot 62 and the right slot 64.

Similarly, the protrusion 48 is secured within the second channel arrangement 57 through the utilization of a retained ball 61 and a connector 55 attaching the protrusion 18 to the ball 61. The ball 61 is retained in place friction and the slight flexibility of the material of the portion 44 of base section 15. In particular, the ball 61 is sized such that it is retained within the second channel arrangement 57 while the member 55 connects the ball 61, and ultimately the second channel arrangement to the protrusion 18. In this way, the ball 61 and protrusion 18 are moved in controlled manner relative to the second channel arrangement 57. That is, the ball 61 moves between the center slot 52, the left slot 66 and the right slot 68 through passageways 58 or 60 to thereby move the protrusion 18 to various positions along the base section 15 adjacent the respective center slot 52, the left slot 66 and the right slot 68. It is appreciated that although the protrusions 16, 18 are connected to one of the balls 59, 61 by its respective connector 53, 55, the protrusions themselves are not physically situated in the slots or passageways. The diameter of the opening for each of the slots is less than the diameter of each of the balls 59, 61, allowing the balls 59, 61 to move between the slots, but yet preventing the balls 59, 61 from being removed from the respective first and second channel arrangements 51, 57.

Each of the protrusions 16, 18 moves in the lateral direction shown by arrows 63, 65, 67, 69 by physically pushing or pulling the protrusions 16, 18 in the proper direction shown by one of the arrows 63, 65, 67, 69. Movement of the balls 59, 61 into the proper slots 50, 62, 64, 52, 66, 68 is confirmed by hearing a sound when the balls 59, 61 are properly in place. The sound is produced by the ball 59 or 61 hitting the exterior portion of one of the slots 50, 62, 64, 52, 66, 68. Alternatively, movement from a narrow passageway to a larger slot can be felt by the user. In either situation, the user will be able to determine that the ball has come to rest in one of the slots. It is noted that each of the protrusions 16,18 can move independently of one another. Typically, the length of each of the passageways 54, 56, 58, 60 can range from 1/16 inch to ¼ of an inch, or any length to achieve the proper arrangement. The lateral movement of one of the protrusions 16, 18 is independent of the movement of the other protrusion.

Figure 6:
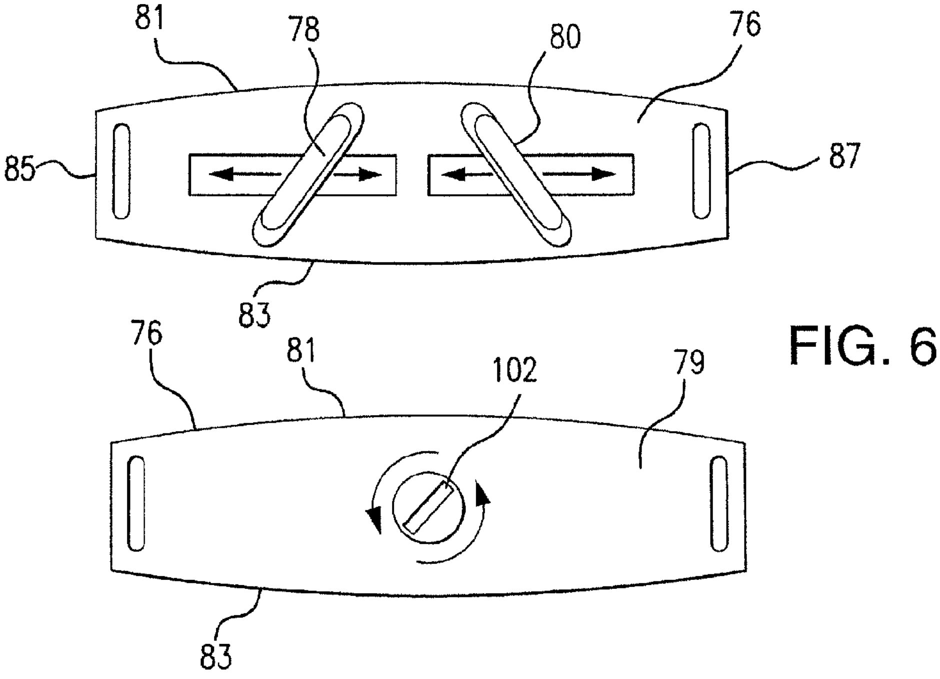
FIG. 6 illustrates a simplified front and back view of the embodiment shown in FIG. 5 provided with an arcuate base instead of a rectangular base.

FIGS. 5 and 6 illustrate an alternate mechanism for changing the position of the protrusions with respect to one another utilizing the rotation of a gear 104. In this embodiment, the protrusions will be mounted on discs. Similar to embodiment shown with reference to FIGS. 3 and 4, protrusions 78, 80 (shown in phantom in FIG. 5), move laterally along the base section 74 under the control of first and second channel arrangements 77, 79 between positions adjacent three different slots. For example, protrusion 78 and disc 111 move along the first channel arrangement 77 between slots 82, 84, 86 under the control of the user and protrusion 80 and disc 113 move along the second channel arrangement 79 between slots 88, 90, 92 under the control of the user.

The device 74 as shown in FIG. 5 includes a base section 76 upon which the protrusions 78, 80 and the position changing device are positioned. As shown in FIG. 5, where the front layer and back layer are removed for the sake of clarity in explaining the invention, protrusions 78, 80 and discs 111 and 113 are provided on the base section 76. Similar to the embodiment shown in FIGS. 3 and 4, the embodiment shown in FIG. 5 is positioned between the front layer 12 and the back layer 14 shown in FIG. 1. The base section 76 is provided with first and second channel arrangements 77, 79 for the retention and movement of the protrusions 78, 80.

The first channel arrangement 77 includes a center slot 82, a left slot 84 and a right slot 86. A passageway 94 is provided between the center slot 82 and the left slot 84. A passageway 96 is provided between the center slot 82 and the right slot 86. Similarly, the second channel arrangement 79 includes a center slot 88, a left slot 92 and a right slot 90. A passageway 98 is provided between the center slot 88 and the left slot 92. A passageway 100 is provided between the center slot 88 and the right slot 90. The protrusion 78 and disc 111 are retained within the first channel arrangement 77 and is therefore moveable under the control of a user between the center slot 82, the left slot 84 and the right slot 86 which are also included on the base section 74. The first protrusion 78 and disc 111 move within the passageway 94 as it moves between the center slot 82 and the left slot 84 under the control of the user. The first protrusion 78 and disc 111 moves within the passageway 96 as it moves between the center slot 82 and the right slot 86 under the control of the user. Similarly, the second protrusion 80 and disc 113 are retained within the second channel arrangement 79 and is therefore moveable under the control of a user between the center slot 88 and a left slot 92, as well as between the center slot 88 and the right slot 90. The second protrusion 80 and disc 113 moves within the passageway 98 as it moves between the center slot 88 and the left slot 92 under the control of the user. The second protrusion 80 and disc 113 moves within the passageway 100 as it moves between the center slot 88 and the right slot 90 under the control of the user.

Similar to the embodiment shown in FIGS. 3 and 4, the protrusions 78, 80 and discs 111, 113 are connected to a ball-like member (not shown) which physically moves between the slots 82, 84, 86, 88, 90, 92 utilizing the various passageways 94, 96, 98, 100.

A gear 104 is provided with a plurality of teeth 106 on its periphery. Alternatively, the periphery of the gear 104 could be smooth. The gear 104 is situated on the base section 76 between slots 86 and 92. A relatively rigid connecting band 108 is connected to the periphery of the gear 104 and disc 111, which in turn is connected to the protrusion 78. Another relatively rigid connecting band 110 is connected to the periphery of the gear 104 and disc 113, which in turn is connected to the protrusion 80. While both of the connecting bands 108 and 110 are relatively rigid, each of the connecting bands 108 and 110 would exhibit some give or play. Additionally, while the gear 104 is circular in shape, other types of gearing arrangements could be employed to move the protrusions 78 and 80 in a lateral direction.

FIG. 6 broadly illustrates the manner in which the protrusions 78 and 80 shown in phantom in FIG. 5 moves in a lateral direction. A slot 102 is provided in the center of the gear 104 and extends through the front surface 79 to the base section 76 as shown in FIG. 6. The insertion of a coin, the end of a screwdriver or a similar device into the slot 102 and the rotation of the coin, screwdriver or other device results in the rotation of the gear 104 in either a clockwise or a counter-clockwise direction. The flexible or rigid connecting band 108 is secured to the periphery of the disc 111. As such, the rotation of the gear 104 results in the lateral movement of the disc 111, which in turn causes the protrusion 78 to move between the slots 82, 84, 86 within the passageways 94, 96. Similarly, the flexible or rigid connecting band 110 is secured to the periphery of the disc 113. The rotation of the gear 104 also results in the lateral movement of the disc 113, resulting in the lateral movement of the protrusion 80 between the slots 88, 90, 92 within the passageways 98 and 100. Since bands 108, 110 are both connected to the gear 104, the rotation of the gear 104 results in the simultaneous lateral movement of both of the discs 111, 113 and consequently, both of the protrusions 78, 80 within the passageways 94, 96, 98, 100.

Assuming the protrusion 78 is in slot 84 and the gear 104 is rotated in the clockwise direction, band 108 moves to the right, forcing the disc 111 and protrusion 78 to move to the right, thereby moving the protrusion 78 from slot 84 through passageway 94 to rest in slot 82. Additionally, movement of the gear 104 in the clockwise direction would result in the disc 111 and the protrusion 78 moving from slot 82 through passageway 96 to rest in slot 86. Simultaneously, band 110 would move to the left forcing the disc 113 and the protrusion 80 to move from slot 90 through passageway 100 to come to rest in slot 88. Additional movement of the gear 104 in the clockwise direction would result in disc 113 and the protrusion 80 moving from slot 88 through passageway 98 and come to rest in slot 92. Therefore, as can be appreciated, movement of the gear 104 in the clockwise direction would result in narrowing the distance between the protrusions 78, 80. For example, if protrusion 78 was initially situated in slot 82 and protrusion 80 was initially situated in slot 88, clockwise movement of the gear 104 would result in protrusion 78 moving from slot 82 to slot 86 and protrusion 80 moving from slot 88 to slot 92. Each of the slots 82, 84 and 86 are provided in a straight line with respect to one another, allowing the protrusion 78 to easily move into these slots along passageways 94 and 96. Similarly, slots 88, 90 and 92 are provided in a straight line with respect to one another, allowing the protrusion 80 to move into these slots along passageways 98 and 100.

When gear 104 is rotated in the counter-clockwise direction, the band 108 moves to the left, causing disc 111 and protrusion 78 to move to the left, thereby forcing protrusion 78 to move from slot 86 through passageway 96 to slot 82 and then through passageway 94 to come to rest in slot 84. Rotation of the gear in the counter-clockwise direction results in the band 110 moving to the right, thereby forcing the disc 113 and the protrusion 80 to move to the right, such that protrusion 80 moves from slot 92 through passageway 98 to slot 88. Additional rotation of the gear in the counter-clockwise direction forces the disc 113 and the protrusion 80 to move from slot 88 through passageway 100 to slot 90. Therefore, as can be appreciated, movement of gear 104 in the counter-clockwise direction results in increasing the distance between the protrusions 78, 80. For example, if protrusion 78 was initially situated in slot 82 and protrusion 80 was initially situated in slot 88, counter-clockwise movement of gear 104 would result in protrusion 78 moving from slot 82 to slot 84 and protrusion 80 moving from slot 88 to slot 90. Apertures 70, 72 would allow the device 74 to be connected to a belt similar to that shown in FIG. 1.

Although FIG. 5 illustrates the base section 76 in the form of a rectangle, it is noted that base section 76 need not be rectangular in shape. For example, as shown in FIG. 6, legs 81 and 83 are slightly arced as they extend between ends 85 and 87. As a matter of fact, the base section 76 can be of any shape without departing from the spirit of the invention. Additionally, the base section 76 is flexible to provide adequate pressure on the target area of the abdomen and to accommodate movement of the patient during treatment.

Figure 7:
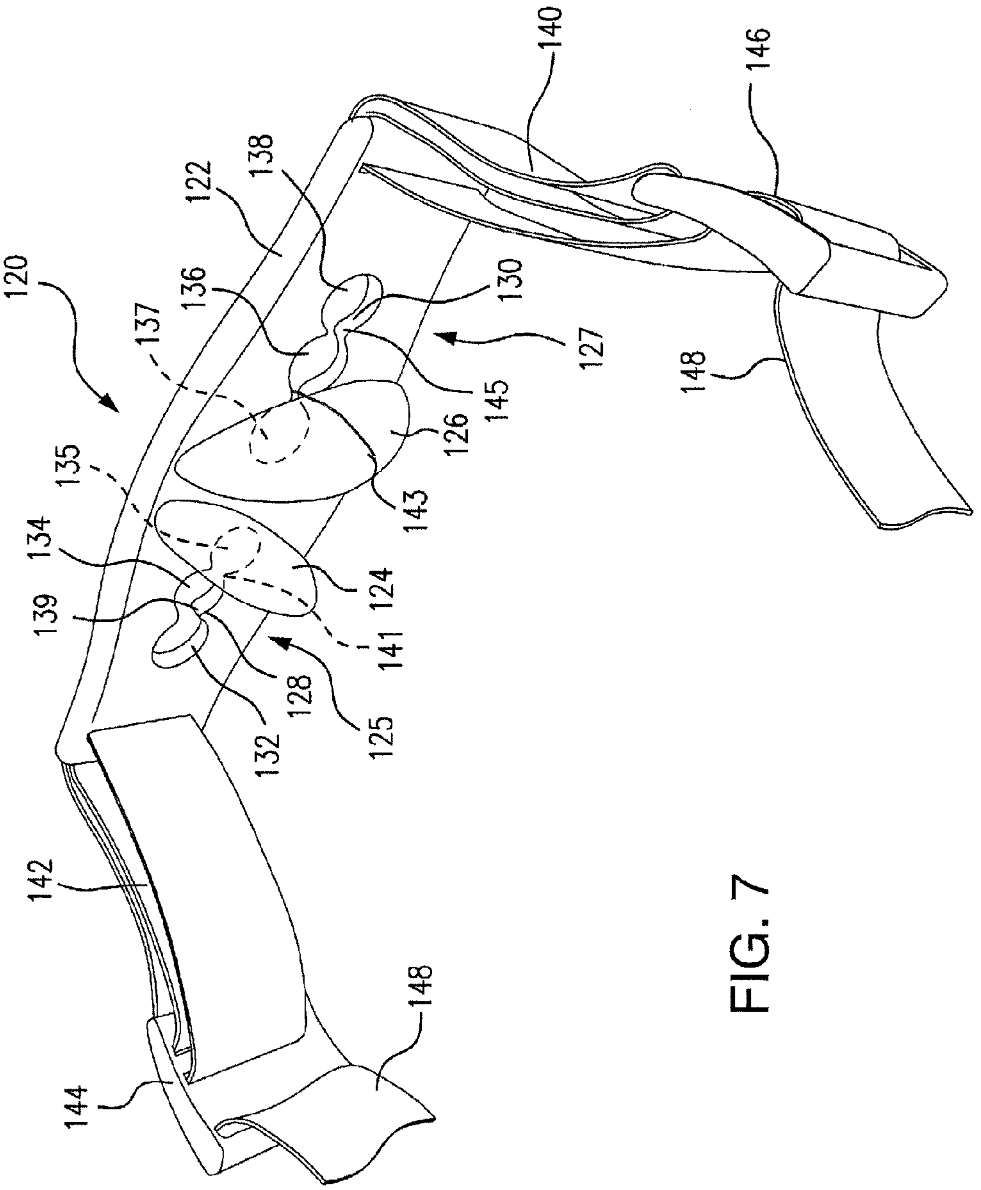
FIG. 7 is a perspective view of a third embodiment of the present device attached to adjustable straps.

FIG. 7 illustrates the invention 120 including a base section 122 provided with protrusions 124, 126 moving a manner similar to the movement of protrusions 16, 18 illustrated in FIGS. 3 and 4. However, it is noted that the base section 122 is not enclosed, and the protrusions 124, 126 directly contact the skin of the patient. The base section 122 is provided with first and second channel arrangements 125, 127 for the retention and movement of the protrusions. The first channel arrangement 125 includes a center slot 134, a left slot 132 and a right slot 135 (hidden from view). A passageway 139 is provided between the center slot 134 and the left slot 132. A passageway 141 (hidden from view) is provided between the center slot 134 and the right slot 135. Similarly, the second channel arrangement 127 includes a center slot 136, a left slot 137 (hidden from view) and a right slot 138. A passageway 143 (hidden from view) is provided between the center slot 136 and the left slot 137. A passageway 145 is provided between the center slot 136 and the right slot 138. The protrusion 124 is retained within the first channel arrangement 125 and is therefore moveable under the control of a user between the center slot 134, the left slot 132 and the right slot 135 which are also included on the base section 122. The first protrusion 124 moves within the passageway 139 as it moves between the center slot 134 and the left slot 132 under the control of the user. The first protrusion 124 moves within the passageway 141 as it moves between the center slot 134 and the right slot 135 under the control of the user. Similarly, the second protrusion 126 is retained within the second channel arrangement 127 and is therefore moveable under the control of a user between the center slot 136 and a left slot 137, as well as between the center slot 136 and a right slot 138. The second protrusion 126 moves within the passageway 143 as it moves between the center slot 136 and the left slot 137 under the control of the user. The second protrusion 126 moves within the passageway 145 as it moves between the center slot 136 and the right slot 138 under the control of the user.

Similar to the embodiment shown in FIGS. 3 and 4, the protrusions 124, 126 are connected to a ball-like member (not shown) that can physically move between the slots 132, 134, 135, 136, 137, 138 utilizing the various passageways 139, 141, 143, 145.

Figure 8:
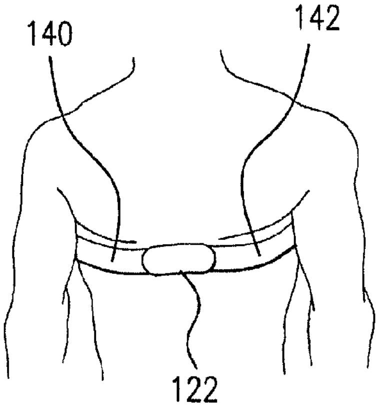
FIG. 8 is a front view of the third embodiment of the present device surrounding the torso of a patient.
Figure 9:
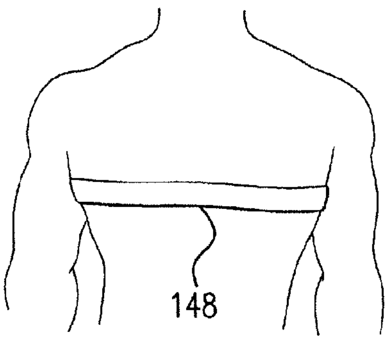
FIG. 9 is a back view of the third embodiment of the present device surrounding the torso of the patient shown in FIG. 8.
Figure 13:
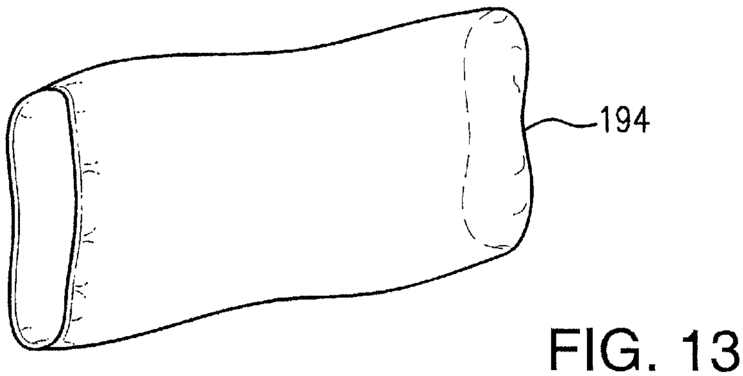
FIG. 13 is a view illustrating an elastic gauze sheath protecting the anti-reflux/heartburn treatment device.

A strap 142 is connected to one side of the center section 122 and a second strap 140 is attached to the second side of the center section 122. The strap 142 is adjustable utilizing the buckles 144, 146. Both of the buckles 144, 146 are connected to a belt 148 for encircling a portion of the patient's torso while situating the center section 122 at the proper location to apply pressure to the appropriate position of the patient's stomach or abdomen as shown in FIGS. 8 and 9. Each of the ends of the belt 148 is adjustably secured to one another through the use of securing device, such as a buckle 150 illustrated in FIG. 8. Additionally, any state of the art connecting device, such as, but not limited to, a hook and loop fastener 184, 186, 190 and 192 as shown in FIG. 13 may be employed. It is noted that the protrusions 124, 126 of the embodiment depicted in FIG. 7 are directly applied to the torso of the patient, and are not positioned between the front layer 12 and the back layer 14 shown in FIG. 1.

The base section is constructed from materials such as foam rubber, silicon or other similar material safe to be used on a patient's skin, as long as the material is fairly rigid. Similar to the previously described protrusions, the protrusions 124, 126 illustrated in FIG. 7 are constructed from a thermoplastic rubber (TPR) material, silicone, a viscoelastic material, or similar material safe to be used on a patient's skin. It is noted that the protrusion shown in FIGS. 3 and 4 can be provided between the front and back layers 12, 14 as shown in FIG. 1 or, similar to the device shown in FIG. 7, the protrusions 16, 18 can be directly applied to the torso of the patient. The protrusions 124, 126 of the device shown in FIG. 7 would directly be applied the torso of the patient.

FIGS. 8 and 9 illustrate the positioning of the device 120 according to the present invention around a patient's torso. As shown in FIG. 8, the straps 140, 142 function to position the base section 122 on the front of the patient. As shown in FIG. 9, therein, the belt 148 wraps around the back of the patient to affix the device 120 for applying pressure to the appropriate position of the patient's body. Although FIGS. 8 and 9 show the anti-reflux/heartburn treatment device 120 applied to the torso of the patient, the devices shown in FIGS. 1-6 can be applied to the torso of the patient in a similar manner.

In another embodiment, proper pressure can be applied to the correct position on a patient's abdomen utilizing a pair of protrusions which are inflated using a device such as a pump. The pump would be employed inflate the protrusions, as well as the base section, thereby effectively increasing or decreasing the pressure applied to the patient's abdomen in a manner to deliver the proper mechanical pressure comfortable to the patient. This embodiment achieves the desired result of reducing the patient's heartburn symptoms without the necessity of laterally moving the protrusions within the endoskeleton to which the protrusions are provided.

Figure 10:
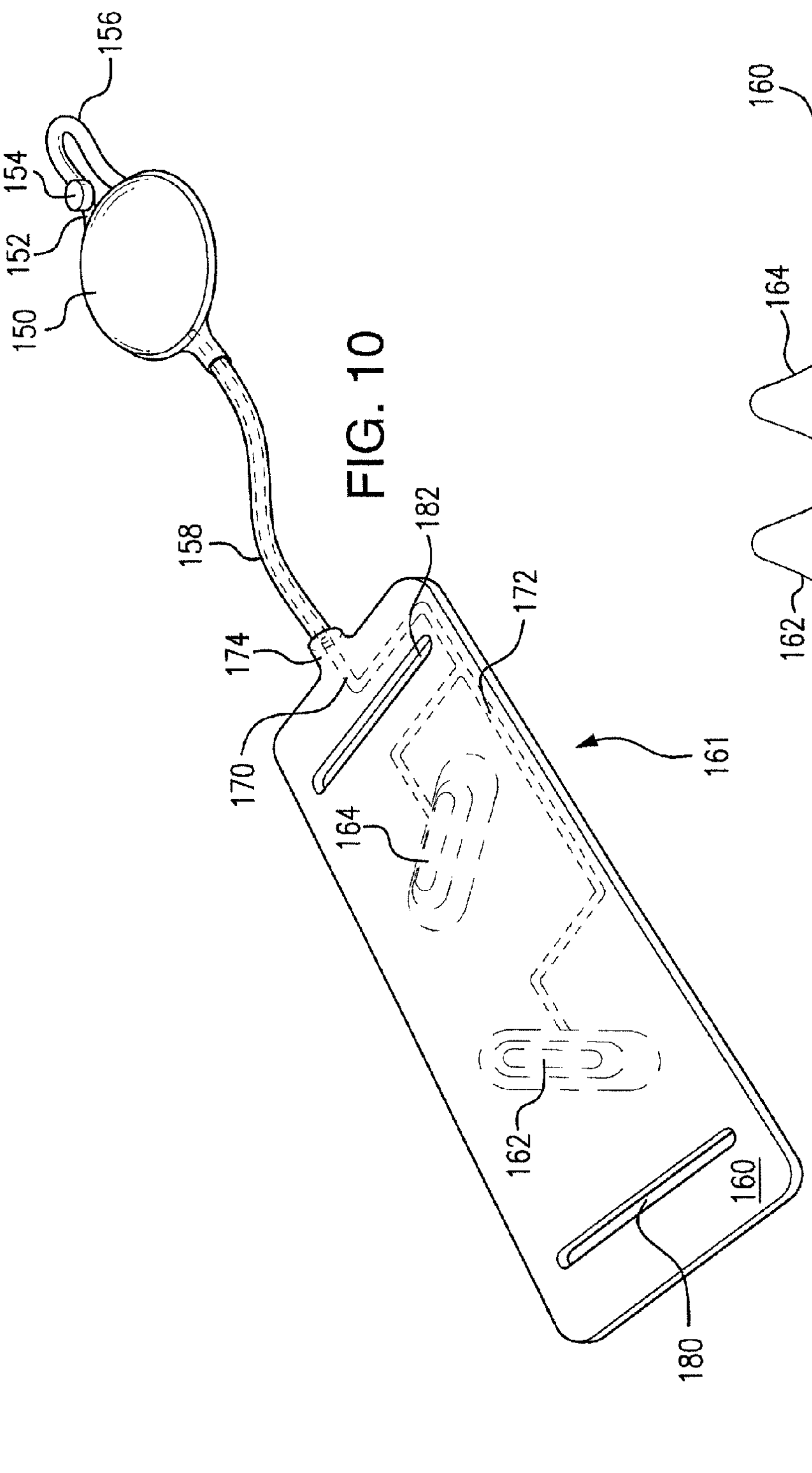
FIG. 10 is a perspective view showing the bladder pump connected to the anti-reflux/heartburn device.
Figure 11:
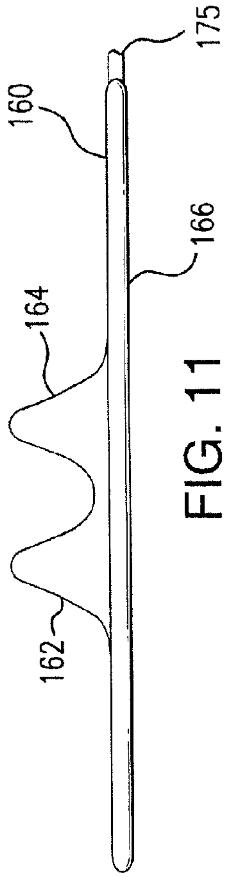
FIG. 11 is a view showing the protrusions connected to a fluid supply with the top and bottom layer of the anti-reflux/heartburn device removed.

Referring to FIGS. 10 and 11, an anti-reflux/heartburn device 161 having two protrusions 162, 164 is provided between a top layer 160 and a bottom layer 166 of a planar base section of the anti-reflux/heartburn device 161. The top surface of each of the protrusions 162, 164 abuts the bottom surface of the top layer 160. An opening is provided on the bottom of each of the protrusions 162, 164. Each of the protrusions 162, 164 is preferably constructed from a plastic or rubber-like material which can expand or contract, when fluid, such as air, is pumped into each of the protrusions or removed from the protrusions.

Air is forced between the top layer 160 and the bottom layer 166 by repeatedly squeezing the exterior surface of a pump 150, thereby forcing air to enter an intake nozzle 152, flow through the pump 150 to a hollow passageway 158, and then to a connector 174 provided between the hollow passageway 158 and the anti-reflux/anti-heartburn device 161. A first channel 170 is provided between the connector 174 and the bottom of the protrusion 164, and is situated between the top layer 160 and the bottom layer 166. A second channel 172 is provided between the first channel 170 and the bottom of the protrusion 162, and is also situated between the top layer 160 and the bottom layer 166. Both of the channels 170 and 172 are provided with small perforations on their outer surface, resulting in both protrusions 162 and 164 being inflated, as well as inflating at least a portion of the area between the top layer 160 and the bottom layer 166. The area between the top layer 160 and the bottom layer is inflated in the range of between one and four millimeters.

An end of the intake nozzle 152 is provided with a one-way valve. An air release valve 154 is attached to an air release hose 156 extending from the end 170 of a passageway included within an ordinary bulb-type the pump 150, such as a blood pressure pump, used to prevent air from exiting the pump 150 during the inflation of the device 161.

When the device 161 is to be inflated, the air release valve 154 is provided with a closure, such as rotating a cap to close off the air release hose 156. Similarly, the cap can be pushed into the air release hose 156 to prevent air from exiting the pump 150. Once the air release valve 154 is closed, the pump 150 is squeezed several times to force air into the intake nozzle 152 and through the one way valve into the interior of the pump 150. The air then moves through the hollow passageway 158 into the device 161, between the top layer 160 and the bottom layer 166, as well as into the protrusions 162, 164, resulting in the inflation of the anti-reflux/anti heartburn device 161. The use of the one way valve prevents air from flowing out from end 168 of the pump 150. During treatment, the hollow passageway 158 is disconnected from the device 161. A sealing device such as a cap 175 or similar closure device is used to close the connector 174 of the anti-reflux/anti-heartburn device 161 to ensure that the anti-reflux/anti-heartburn device remains inflated. The anti-reflux/heartburn device 161 is then attached to the belt 148 shown in FIGS. 8 and 9 using apertures 180, 182 provided in the device 161, and then applied to the proper location near the patient's abdomen. As is true with all of the embodiments, the belt 148 is placed around the mid thoracic spine for proper placement of the device at the upper abdominal area of the xyphoid process level. The two protrusions 162, 164 are located in the same oblique position, and would press against the patient's upper abdomen.

After use, the protrusions 162, 164 are deflated by removing the cap 175 or similar closure device from the connector 174, allowing the air to be drained from the protrusions 162, 164 as well as between top layer 160 and the bottom layer 166 of the anti-reflux/heartburn device 161. When the device is to be re-inflated, the connector 174 is reconnected to the hollow passageway 158 attached to the pump 150 and the process of inflating the protrusions 162, 164 as well as the area between the top layer 160 and the bottom layer 166 of the anti-reflux/heartburn device 161 is repeated. This particular configuration allows the protrusions 162, 164 to be inflated to a first level for one patient and to a second level, different than the first level, for another patient based upon the amount of air pumped into the anti-reflux/heartburn device 161. Some patients would require that the protrusions 162, 164 and the area between the bottom layer 160 and the top layer 166 be inflated to a maximum size to obtain relief. Other patients would require that the protrusions 162, 164 and the area between the top layer 160 and the bottom layer 166 need not be inflated to a maximum level to obtain relief.

Additionally, although the pump 150 has been described as inflating two protrusions, the pump 150 could operate to inflate only a single protrusion provided between the top layer of material 160 and the bottom layer of material 166 of the anti-reflux/heartburn device 161, as well as inflate three or more protrusions.

Figure 12:
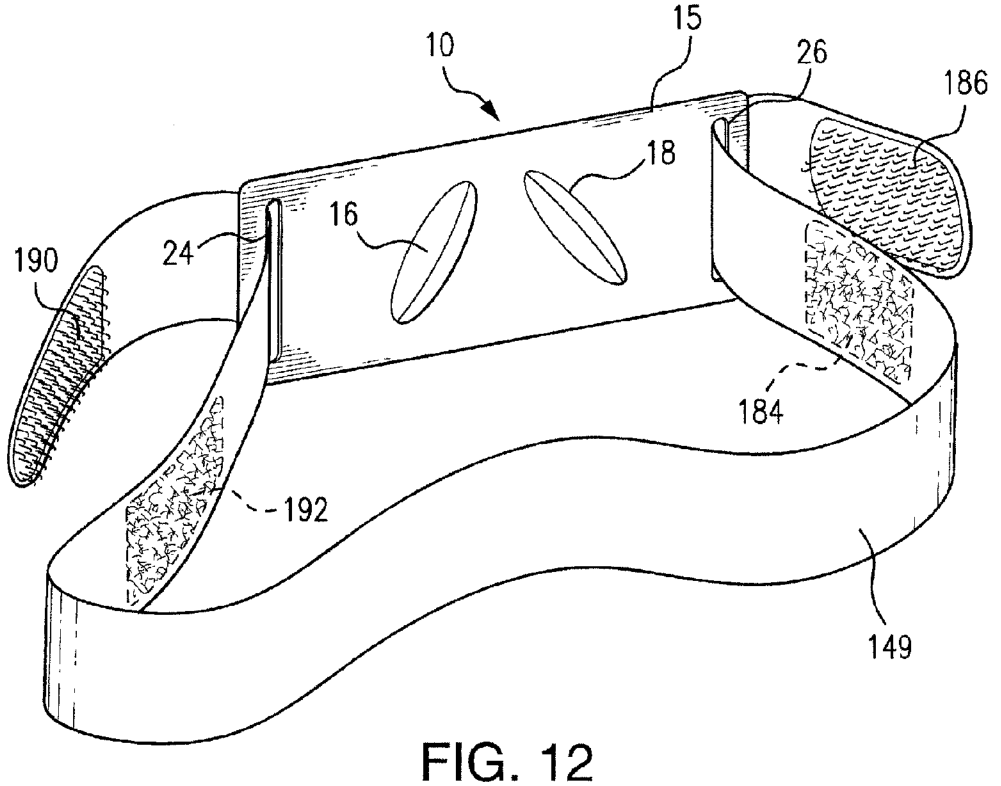
FIG. 12 is a perspective view of the present invention shown in FIG. 1 attached to an adjustable belt.

FIG. 12 illustrates one manner of securing the invention 10 including the base section 15 provided with protrusions 16 and 18 to the belt 149 through apertures 24 and 26. A first end of the belt 148 includes hook and loop closures 184 and 186 cooperating with one another to secure the first end of the belt 149 to the base section 15. Hook and loop closures 190 and 192 are provided on the second end of the belt 148 to secure the second end of the belt 149 to the base section 122. The use of the hook and loop closures 184, 186, 190 and 192 enable the length of the belt 148 to be adjustable. For ease of explanation, the device 10 in FIG. 12 is shown without front cover 12 and the protrusion changing device.

Each of the protrusions could include a vibratory circuit provided with a source of power, such as a small rechargeable battery and an on/off switch. When the switch is in the on position, a circuit would be completed and the material would vibrate, thereby producing a therapeutic sensation at the pressure point(s).

Since the anatomical point in which the device is placed overlaps a series of acupuncture points along meridians which affect gastro function, pressure and/or "needling" along these points have been known to calm and/or reduce gastric symptoms including, but not limited to, gastroesophageal reflux or heartburn. Therefore, it is believed that the affects of the pressure delivered by the present invention would elicit a similar response as achieved by acupuncture or acupressure.

Since it is important to properly place the protrusion(s) on the appropriate points of a patient's abdomen it is important to provide a device which can be easily adjusted when the device is initially placed around a patient's torso prior to securing the device around the torso to apply the proper pressure at a particular point on the patient's abdomen. The present invention is provided with two protrusions for the purpose of applying pressure to the appropriate points on the patient's body. The protrusions are generally provided on a base section of the device which is attached on both ends to a strap for encircling the patient's torso. The base section may be a planar rigid material having first and second ends provided with a device for changing the position of the protrusions on the planar rigid material prior to the device encircling the patient's torso. The position of the protrusions can also be adjusted after the device encircles the patient's torso.

The protrusions would be preferably constructed from a semi-dense foam, silicon material or a viscoelastic material, or any other semi-rigid material that would serve the same purpose. Viscoelastic materials provide a relationship between stress and strain dependent upon time. These materials have a unique equilibrium configuration which can ultimately recover fully after the removal of a transient load. Each of the protrusions can be provided with an interior endoskeleton allowing for more rigidity. Alternatively, the endoskeleton need not be provided in the interior of the protrusion. The protrusions can also be constructed from a plastic or rubber-like material, allowing the protrusions to expand and contract when a fluid such as air flows into and out of the protrusions.

Figure 14:
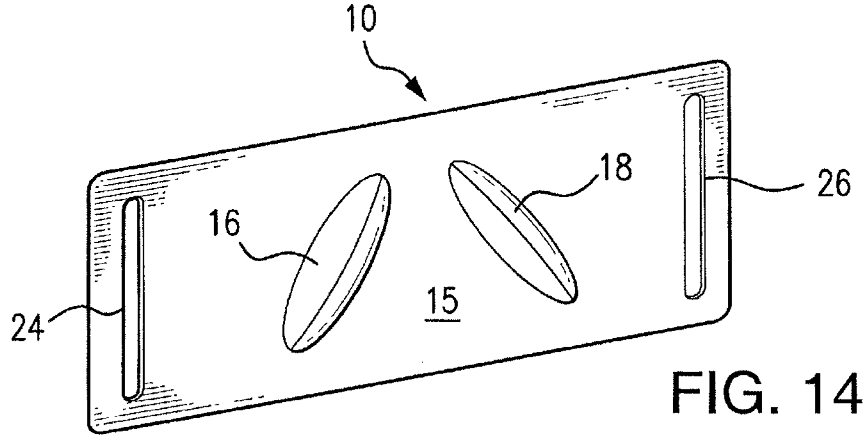
FIG. 14 is a view showing the anti-reflux/heartburn treatment device without an elastic gauze sheath.
Figure 15:
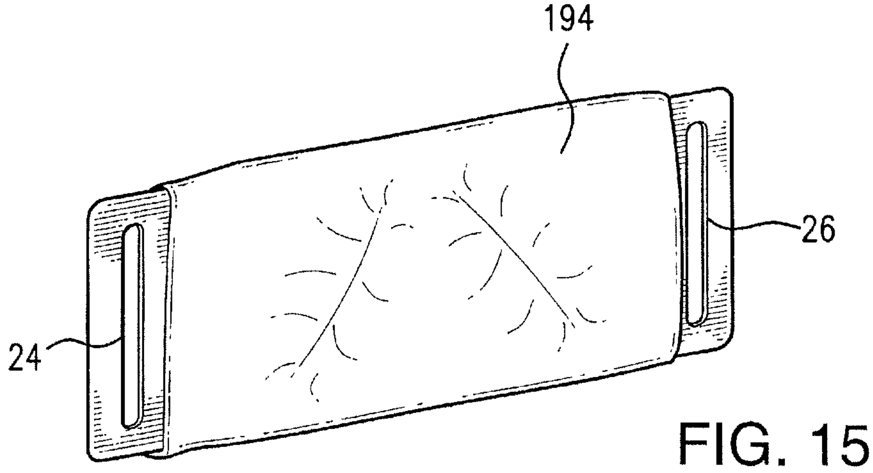
FIG. 15 is a view showing the anti-reflux/heartburn treatment device inserted into the elastic gauze sheath.

FIGS. 13-15 show the use of a flexible sheath 194 used to cover and add increased comfort to the anti-reflux/heartburn treatment device when in use. In addition, the sheath keeps the device free from the skin cells, oil and dirt. The sheath is disposable after several uses and a new sheath is then added. Before treatment using the anti-reflux/heartburn treatment device has occurred, the belt 40 is removed from the anti-reflux/heartburn treatment device 10 by removing the belt 40 through the apertures, such as 24, 26 and re-attaching the strap 40 prior to application. The anti-reflux/heartburn treatment device 10, as shown, for example, in FIG. 14, is inserted into the cylindrical shaped sheath 194 covering the protrusions 16, 18 of the base section 15, as illustrated in FIG. 14, resulting in the anti-reflux/heartburn treatment device shown in FIG. 15. The sheath 194 can be constructed from any elastic-like material, such as, but not limited to stocking gauze constructed from spandex or lycra. The particular stocking gauze used to cover the device 10 can be replaced after each use. For ease of explanation, device 10 in FIG. 15 is shown without front cover 12 and the protrusion changing device.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A method for treating anti-reflux/heartburn, comprising:

applying mechanical pressure to a patient's body by a device that encircles a patient's torso, the device including a planar base section provided with first and second ends, a band which is adjustable in length attached to the first and second ends, and first and second protrusions provided on the planar base section; the first and second protrusions are separated from one another and are elongated so as to include a long axis substantially parallel to the plane in which the planar base section lies to define a length of each of the first and second protrusions and a short axis substantially parallel to the plane in which the planar base section lies to define a width of each of the first and second protrusions;

adjusting the first and second protrusions so as to be positioned on a patient's stomach at anatomical points which overlap a series of acupuncture points along meridians which affect gastro functions of the patient; and adjusting the length of the band to apply said mechanical pressure.

* * * * *